(12) United States Patent
Ritter (10) Patent No.: US 11,819,597 B2
(45) Date of Patent: Nov. 21, 2023

(54) DIALYZER AND DIALYSIS APPARATUS

(71) Applicant: B. Braun Avitum AG, Melsungen (DE)

(72) Inventor: Kai-Uwe Ritter, Melsungen (DE)

(73) Assignee: B. Braun Avitum AG, Melsungen (DE)

( * ) Notice: Subject to any disclaimer, the term of this patent is extended or adjusted under 35 U.S.C. 154(b) by 174 days.

(21) Appl. No.: 17/433,914

(22) PCT Filed: Feb. 24, 2020

(86) PCT No.: PCT/EP2020/054736
§ 371 (c)(1),
(2) Date: Aug. 25, 2021

(87) PCT Pub. No.: WO2020/173857
PCT Pub. Date: Sep. 3, 2020

(65) Prior Publication Data
US 2022/0133969 A1    May 5, 2022

(30) Foreign Application Priority Data
Feb. 26, 2019    (DE) ................ 10 2019 104 837.0

(51) Int. Cl.
*A61M 1/16* (2006.01)
*A61M 1/36* (2006.01)

(52) U.S. Cl.
CPC ........ *A61M 1/1621* (2014.02); *A61M 1/3635* (2014.02); *A61M 2205/7536* (2013.01)

(58) Field of Classification Search
None
See application file for complete search history.

(56) References Cited

U.S. PATENT DOCUMENTS 4,293,413 A * 10/1981 Schnell ............... A61M 1/3627
                                                210/321.78
4,784,768 A * 11/1988 Mathieu ................ B01D 63/04
                                                210/336

(Continued)

FOREIGN PATENT DOCUMENTS

DE      19728071 A1      2/1999
EP       1532994 A1 *    5/2005 .......... A61M 1/1008
JP      2010166970 A     8/2010

OTHER PUBLICATIONS

Written Opinion received in International Application No. PCT/EP2020/054736 dated Jun. 9, 2020, with translation, 12 pages.

(Continued)

*Primary Examiner* — Krishnan S Menon
(74) *Attorney, Agent, or Firm* — Christopher A. Rothe; Culhane Meadows PLLC (57) ABSTRACT

A dialyzer for an extracorporeal blood treatment includes an elongated, preferably cylindrical dialyzer housing, and at least one dialysis membrane that separates an internal space of the dialyzer housing into a dialysis liquid chamber and a blood chamber. The dialysis liquid chamber has a dialysis liquid supply port and a dialysis liquid discharge port. The blood chamber has a blood supply port and a blood discharge port. The dialyzer includes an additional ventilation outlet for ventilating the blood chamber. The additional ventilation outlet is located with respect to a blood flow direction in the blood discharge port between an exit area of the blood discharge port and the dialysis liquid supply port. A corresponding dialysis device includes a ventilation outlet on a dialyzer housing or on a hose connected to a blood discharge port.

12 Claims, 6 Drawing Sheets

(56) References Cited

U.S. PATENT DOCUMENTS

2007/0102340 A1* 5/2007 Stillig .............. A61M 1/1625
                                                          210/321.79
2009/0084720 A1   4/2009 Dannenmaier et al.
2015/0367062 A1  12/2015 Brugger et al.

OTHER PUBLICATIONS

Search Report received in German Application No. 10 2019 104 837.0 dated Nov. 19, 2019, with translation, 14 pages.
Search Report received in International Application No. PCT/EP2020/054736 dated Jun. 9, 2020, with translation, 5 pages.
Office Action received in Chinese Application No. 202080016892.8 dated Jun. 16, 2023, with translation, 16 pages.

* cited by examiner

DIALYZER AND DIALYSIS APPARATUS

CROSS-REFERENCE TO RELATED APPLICATIONS

This application is the United States national phase entry of International Application No. PCT/EP2020/054736, filed Feb. 24, 2020, and claims the benefit of priority of German Application No. 10 2019 104 837.0, filed Feb. 26, 2019. The contents of International Application No. PCT/EP2020/054736 and German Application No. 10 2019 104 837.0 are incorporated by reference herein in their entireties.

FIELD

The present invention relates to a dialyzer for an extracorporeal blood treatment, comprising an elongated dialyzer housing, at least one dialysis membrane which separates an internal space of the dialyzer housing into a dialysis liquid chamber provided with two dialysis liquid ports and a blood chamber provided with two blood ports. The invention further relates to a dialysis device comprising such a dialyzer.

BACKGROUND

Known dialyzers generally have four ports, with which they can be connected to a dialysis machine line system, on the one hand, and to an extracorporeal blood system connected to a patient, on the other hand. The aforementioned ports are divided into two ports for connection to the extracorporeal blood system or blood circulation via which blood to be purified is conveyed to and from the dialyzer, hereinafter also referred to as blood supply port and blood discharge port, and two ports for connection to the dialysis machine via which dialysis liquid is conveyed to and from the dialyzer, hereinafter also referred to as dialysis liquid supply port and dialysis liquid discharge port.

Before starting a blood treatment method, it is necessary to fill (the so-called priming) the extracorporeal blood circulation including the dialyzer filter with a liquid in order to remove the air present in the extracorporeal circulation. Saline solution is mainly used for this purpose. Alternatively, an ultrapure dialysis liquid is also used, especially in so-called online machines with two dialysis liquid filters and direct connection to a central dialysis liquid supply. When filling with saline solution, a prefilled bag containing saline solution is manually connected to the arterial blood hose end. The blood pump of the dialysis machine then pumps the liquid through the extracorporeal blood circuit. The saline solution finally exits at the venous end of the blood hose. When a sufficient amount of liquid has been circulated, the extracorporeal circulation is filled and thus prepared for blood treatment.

When filling the blood side of the dialyzer, the air must be replaced by dialysis liquid or saline solution. During this process, many individual air bubbles escape which must be flushed out of the interior of the fibers of the dialyzer. Various methods are used to remove this air. For example, the dialyzer can be turned manually, one may tap against the dialyzer or pressure surges can be produced in an automatic preparation procedure. The escaping air enters the outlet-side blood hose of the dialyzer and is separated only in the venous drip chamber, resulting in an undesirable level reduction. This level reduction must be corrected in a further step.

SUMMARY

The task of the present invention is to provide a dialyzer or a dialysis machine that enables a simpler, faster and/or more reliable preparation prior to a blood treatment.

A dialyzer according to the invention for an extracorporeal blood treatment comprises an elongated, preferably cylindrical dialyzer housing and at least one dialysis membrane. The dialysis membrane separates an internal space of the dialyzer housing into a dialysis liquid chamber provided with two dialysis liquid ports (a dialysis liquid supply port and a dialysis liquid discharge port) and into a blood chamber provided with two blood ports (a blood supply port and a blood discharge port). The dialysis liquid ports are especially designed as Hansen connectors and the blood ports are especially designed as Luer connectors or glued to the blood hose system.

The dialyzer also has an additional ventilation outlet for ventilating the blood chamber, which is formed on the dialyzer housing on or close to an end face thereof. Preferably, the ventilation outlet can be closed by an air-permeable ventilation membrane. In particular, this ventilation membrane may be formed to be waterproof (hydrophobic). The ventilation outlet or ventilation membrane allows air previously present in the blood chamber to escape when filling the blood chamber with an aqueous liquid, until the blood chamber is completely filled with the liquid. The different permeability of the ventilation membrane with respect to air and aqueous liquid is achieved by the size of pores provided in the ventilation membrane. Preferably, these pores have a diameter less than or equal to 0.2 so that the ventilation membrane at the same time serves as a sterile barrier that prevents germs from entering the blood. In particular, the dialyzer may be configured such that no membrane, in particular no dialysis membrane, is provided In particular, the dialyzer may be designed in such a way that (fluid mechanically or along flow lines) no membrane, in particular not the dialysis membrane, is provided between the additional ventilation outlet and the blood chamber or between the ventilation membrane of the additional ventilation outlet and the blood chamber.

The provision of the ventilation outlet or the ventilation membrane enables a direct escape of the air from the blood chamber into the environment of the dialyzer. This direct escape of the air shortens the flow paths of the escaping air and thus reduces the probability that individual dissolved air bubbles will adhere to other surface areas when flushed out. Furthermore, the shortened flow paths result in faster air removal. Finally, the drop in the level in the venous drip chamber is at least reduced, so that the correction of this level will take at least less time.

The ventilation outlet or ventilation membrane is provided with respect to a blood flow direction in the blood discharge port between an exit area of the blood discharge port and the dialysis liquid supply port.

When preparing a dialysis device for blood treatment, the blood circulation is first filled with liquid before the dialysis liquid circulation is filled with a liquid. This means that during the filling of the bloodstream air can escape from the blood circulation or from the blood chamber into the dialysis circuit or the dialysis liquid chamber also via the semipermeable dialysis membrane, which is impermeable to larger protein molecules such as albumin but permeable to aqueous solutions and air. However, this is especially true for air or air bubbles located in the blood chamber between a blood supply port and the dialysis liquid supply port. In order to also remove air bubbles located between the dialysis liquid supply port and the exit area of the blood discharge port as quickly and reliably as possible, it is advantageous to provide the ventilation outlet or ventilation membrane in this area of the blood chamber.

The dialyzer housing according to the invention can have a dialyzer cap on which the ventilation outlet or ventilation membrane is provided. Known dialyzers have a housing with a central, hollow cylindrical portion and two dialyzer caps each arranged at an end of the hollow cylindrical portion. If the ventilation membrane is provided on at least one of the dialyzer caps, it is advantageously possible to continue using the tools used to manufacture the hollow cylindrical portions. It is also easily possible to adapt the dialyzer only by changing the dialyzer caps according to an intended orientation of the dialyzer during operation in a dialysis device.

The ventilation outlet or ventilation membrane can be provided at the blood discharge port. In other words, the ventilation outlet can branch off from a nozzle of the blood discharge port. If the ventilation outlet or the ventilation membrane is provided in the blood flow direction at the end of the blood side of the dialyzer, it is possible to almost completely remove the air present in the blood chamber before filling.

The dialyzer housing may be provided with a ventilation nozzle to which a closure for air-tight sealing of the ventilation outlet or ventilation membrane can be attached. By means of this ventilation nozzle, the position of the ventilation outlet or ventilation membrane can be advantageously displayed to a person installing the dialyzer on a dialysis device. By attaching a closure, for example in the form of a Luer cap, any pathogens can be prevented from entering after the priming of the dialysis device.

The ventilation outlet or ventilation membrane can be formed so as to annularly surround the blood discharge port. Thus, regardless of the orientation of the dialyzer around an axis of extension of the blood discharge port, a constant quality of the air removal from the dialyzer can be ensured.

The ventilation membrane may have an at least double-ply design. A first ply of the ventilation membrane, in particular facing the blood chamber or an interior of the blood chamber, can be formed so as to be hydrophobic and a second ply of the ventilation membrane, in particular facing away from the blood chamber or an environment, can be formed to be a sterile barrier. In particular, the first ply can be spaced from the second ply. By this dual design, the ventilation membrane can easily be optimized with respect to its water impermeability, on the one hand, and with respect to its sterile barrier property on the other hand.

In particular, the first ply of the ventilation membrane may have larger pores and a smaller surface area than the second ply of the ventilation membrane. In other words, the surface area of the second ply may be larger than the surface area of the first ply. In particular, the pores of the first ply and the pores of the second ply may overlap. If the surface area of the second ply serving as a sterile barrier is formed to be larger than the first ply which is responsible for water impermeability, a high pressure loss can be avoided despite the smaller pores in the second layer.

This present invention also relates to a dialysis device provided with a dialyzer according to the invention.

The dialyzer may be attached to the dialysis device in such a way that the ventilation outlet or ventilation membrane, when the dialysis device is installed ready for operation, is arranged so as to be at least partially above the dialysis liquid supply port in the direction of gravitational acceleration.

As explained above, air bubbles present in the blood chamber between a blood supply port and the dialysis liquid supply port before priming can also escape through the dialysis membrane. In order to also remove air bubbles between the dialysis liquid supply port and the exit area of the blood discharge port, it is advantageous to provide the ventilation membrane in this area of the blood chamber.

The dialyzer may be attached to the dialysis device in such a way that the ventilation outlet or ventilation membrane, when the dialysis device is installed ready for operation, is arranged so as to be at least partially above the blood chamber in the direction of gravitational acceleration.

If the ventilation outlet or ventilation membrane is positioned at least partially above the blood chamber, an at least almost complete removal of the air from the blood chamber is possible.

Alternatively, the dialysis device according to the invention may also comprise a generic dialyzer for an extracorporeal blood treatment, which is provided with an elongated, preferably cylindrical dialyzer housing, at least one dialysis membrane, which separates an internal space of the dialyzer housing into a dialysis liquid chamber provided with a dialysis liquid supply port as well as a dialysis liquid discharge port and into a blood chamber provided with a blood supply port and a blood discharge port. A dialysis device equipped in this way is distinguished by a waterproof and air-permeable ventilation membrane which forms a surrounding wall of the blood drainage hose in at least one portion. Thus, when the blood chamber is filled with a liquid, air that has been previously present in the blood chamber can escape through the ventilation membrane until the blood chamber is completely filled with the liquid. The ventilation membrane of the dialysis device according to the invention has pores whose diameter preferably is smaller than or equal to 0.2 µm in order to be able to serve as a sterile barrier.

If the ventilation membrane is located in the surrounding wall of the blood discharge hose connected to the dialyzer, improved ventilation of a conventional dialyzer can be achieved.

The dialysis devices according to the invention can be designed in such a way that the corresponding dialyzer is attached to the dialysis device such that a liquid conveyed through the blood chamber flows diametrically opposed to gravitational acceleration. In other words, the dialyzer can be attached to the dialysis device in such a way that it extends in vertical direction if the dialysis device is mounted upright on a horizontal plane.

If the buoyancy force of air bubbles in the blood chamber against water in the earth's gravitational field is used to remove them, a more reliable and faster air removal can be achieved.

Alternatively, the dialyzer can also be attached to the dialysis device in such a way that a liquid conveyed through the blood chamber flows perpendicular to the gravitational acceleration. In other words, the dialyzer can be attached to the dialysis device in such a way that it extends in horizontal direction if the dialysis device is mounted upright on a horizontal plane.

BRIEF DESCRIPTION OF THE DRAWING FIGURES

The present invention is described in more detail below using preferred exemplary embodiments with reference to the attached drawings in which.

Identical or functionally equivalent features are provided in the individual Figures with the same reference numerals, wherein the reference numerals of the second, third, fourth and fifth embodiment are marked with . . . ', . . . ", . . . '" and . . . "".

DETAILED DESCRIPTION

Figure 1:
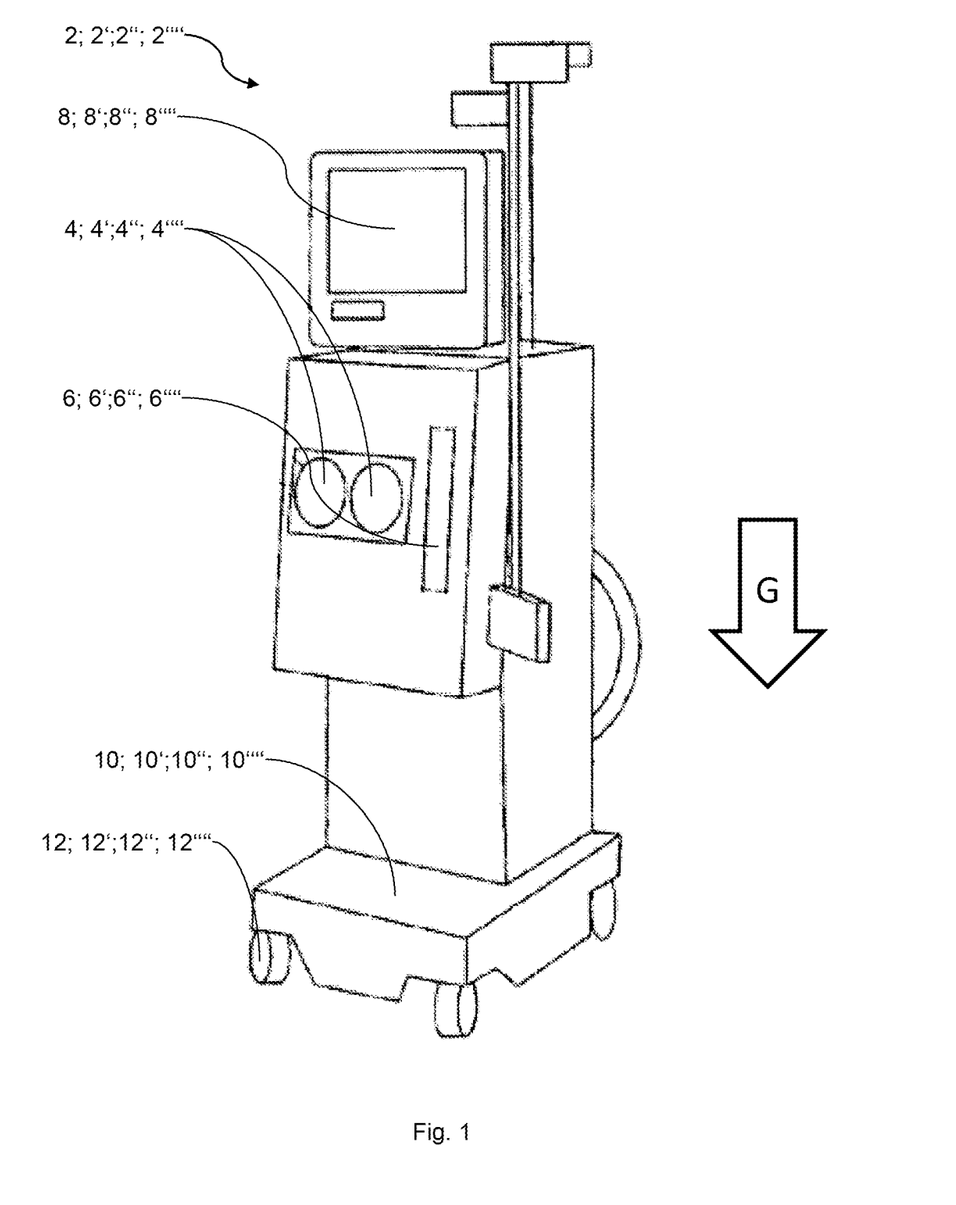
FIG. 1 shows a perspective schematic drawing of a generic dialysis device with a vertically arranged dialyzer.
Figure 6:
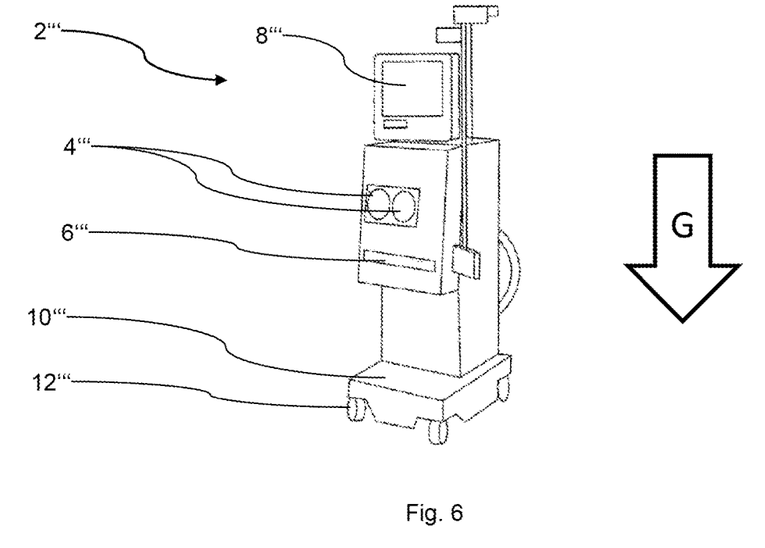
FIG. 6 shows a perspective schematic drawing of a generic dialysis device with a horizontally arranged dialyzer.

A generic dialysis device 2; 2'; 2"; 2'" has peristaltic pumps 4; 4'; 4"; 4'" on a front side for pumping blood and dialysis liquid. A dialyzer 6; 6'; 6"; 6'" is provided near the pumps 4; 4'; 4"; 4'". During operation, the dialyzer 6; 6'; 6"; 6'" is connected to the dialysis device 2; 2'; 2"; 2'", on the one hand, and to a patient on the other hand via (not shown) hoses. One of the pumps 4; 4'; 4"; 4'" delivers blood to be purified to the dialyzer 6; 6'; 6'"; 6'". The other of the two pumps 4; 4'; 4"; 4'" delivers dialysis liquid to the dialyzer 6; 6'; 6'"; 6'". In order to be able to operate the dialysis device 2; 2'; 2"; 2'", a monitor 8; 8'; 8"; 8'" preferably realized as a touchscreen is provided on the front side thereof. To ensure that the dialysis device 2; 2'; 2"; 2'" has a stable and upright position on a horizontal plane, it has a base part 10; 10'; 10'"; 10"" on the underside. To be easy to transport as well, castors 12; 12'; 12"; 12"" are provided on the underside of the base part 10; 10'; 10"; 10"". With the dialysis device 2; 2'; 2"; 2"" shown in FIG. 1, the dialyzer 6; 6'; 6"; 6"" is mounted vertically. As shown in FIG. 6, the dialysis machine 2'" can also be designed such that the dialyzer 6'" extends horizontally.

Figure 2:
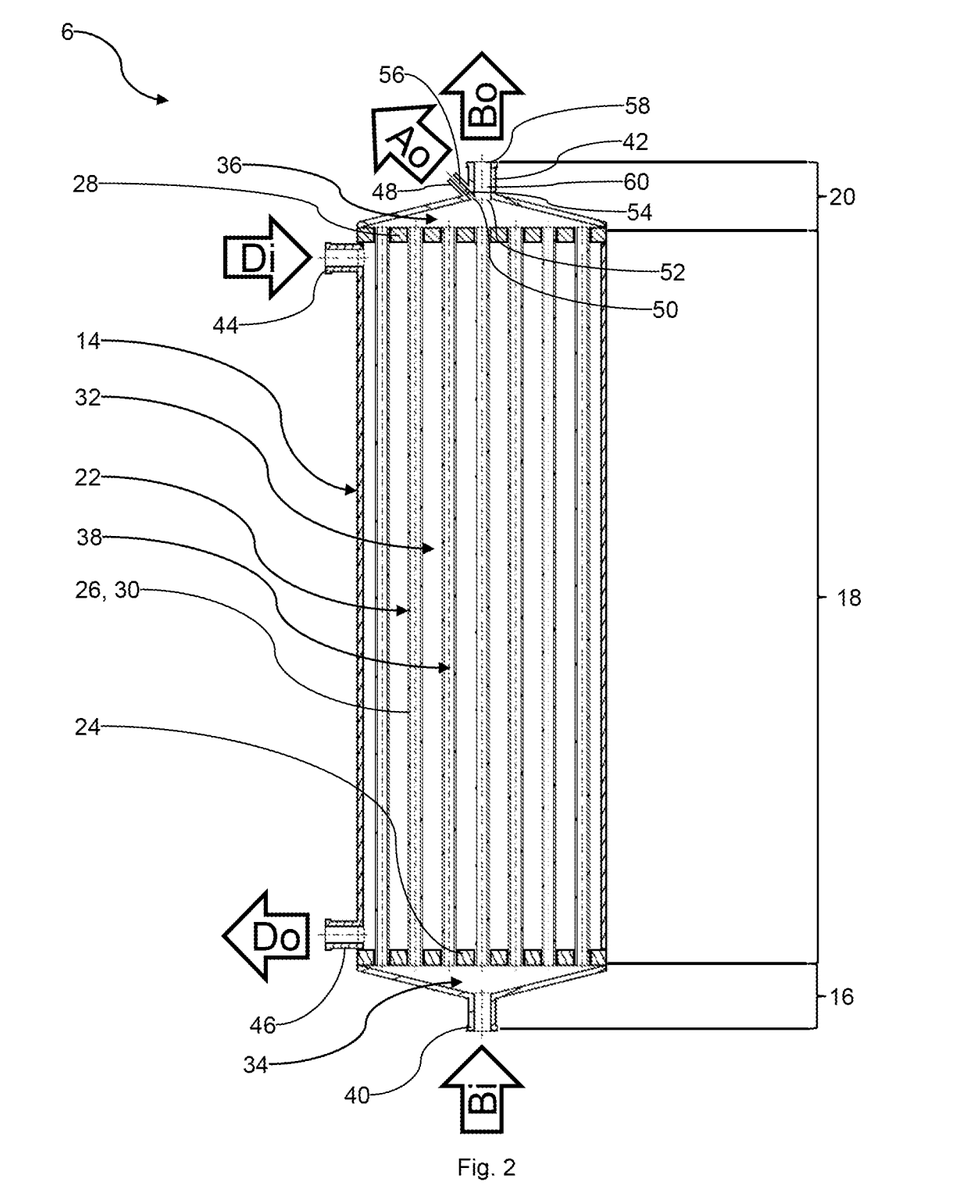
FIG. 2 shows a sectional drawing of a dialyzer of the invention according to a first embodiment.

FIG. 2 shows a sectional drawing of a dialyzer 6 of the invention according to a first embodiment. The dialyzer 6 has a dialyzer housing 14, which can be divided into a lid-shaped blood inlet dialyzer cap 16, an essentially cylindrical, in particular circular cylindrical dialysis liquid section 18 and a likewise lid-shaped blood outlet dialyzer cap 20.

A hollow fiber bundle section 22 is embedded in the dialysis liquid section 18 of the dialyzer housing 14. The hollow fiber bundle section 22 is formed from a first, in particular round, hollow fiber bundle mount 24 in which the one ends of hollow fibers 26 are potted, a hollow fiber bundle consisting of the hollow fibers 26 arranged parallel to one another, and from a second, in particular round, hollow fiber bundle mount 28 in which the other ends of the hollow fibers 26 are potted. The hollow fiber filter module 22 is thus potted at the ends, mounted with the potting material and, if necessary, cut off at the two ends after potting in order to make any accidentally clogged hollow fibers 26 accessible again. The surrounding walls of the individual hollow fibers 26 represent a dialysis membrane 30. The dialysis membrane 30 has pores whose size is adapted such that the dialysis membrane 30 is permeable to water, but impermeable to larger protein molecules such as albumin.

Around the space of the hollow fiber bundle section 22 spanned between the two hollow fiber bundle mounts 24 and 28, the dialysis liquid section 18 of the dialyzer housing 14 extends, the former having in particular a shell-like, circularly cylindrical shape. The space between the hollow fibers 26, which is enclosed by the two hollow fiber bundle mounts 24 and 28 as well as the dialysis liquid section 18 of the dialyzer housing 4, corresponds to a dialysis liquid chamber 32.

The lid-shaped blood inlet dialyzer cap 16 of the dialyzer housing 14 is arranged or attached to the first hollow fiber bundle mount 24 on its side facing away from the hollow fiber bundle section 22 in such a way that a blood distribution space 34 can be defined between the blood inlet dialyzer cap 16 and the first hollow fiber bundle mount 24.

The lid-shaped blood outlet dialyzer cap 20 of the dialyzer housing 14 is arranged or attached to the second hollow fiber bundle mount 28 on its side facing away from the hollow fiber bundle section 22 in such a way that a blood collection space 36 can be defined between the blood outlet dialyzer cap 20 and the second hollow fiber bundle mount 28.

The blood distribution space 34, the space inside the hollow fibers 26 and the blood collection space 36 together correspond to a blood chamber 38 of the dialyzer 6.

A blood supply port 40 for supplying blood (see arrow "Bi" in FIG. 2) is provided on the blood inlet dialyzer cap 16 of the dialyzer housing 14. A blood discharge port 42 for the discharge of blood (see arrow "Bo" in FIG. 2) is provided on the blood outlet dialyzer cap 20 of the dialyzer housing 14. A dialysis liquid supply port 44 for supplying dialysis liquid into the dialysis liquid chamber 32 (see arrow "Di" in FIG. 2) is provided on the dialysis liquid section 18 of the dialyzer housing 14 near the second hollow fiber bundle mount 28. In the vicinity of the first hollow fiber bundle mount 24, a dialysis liquid discharge port 46 for discharging dialysis liquid (see arrow "Do" in FIG. 2) is provided on the dialysis liquid section 18 of the dialyzer housing 14.

Figure 3:
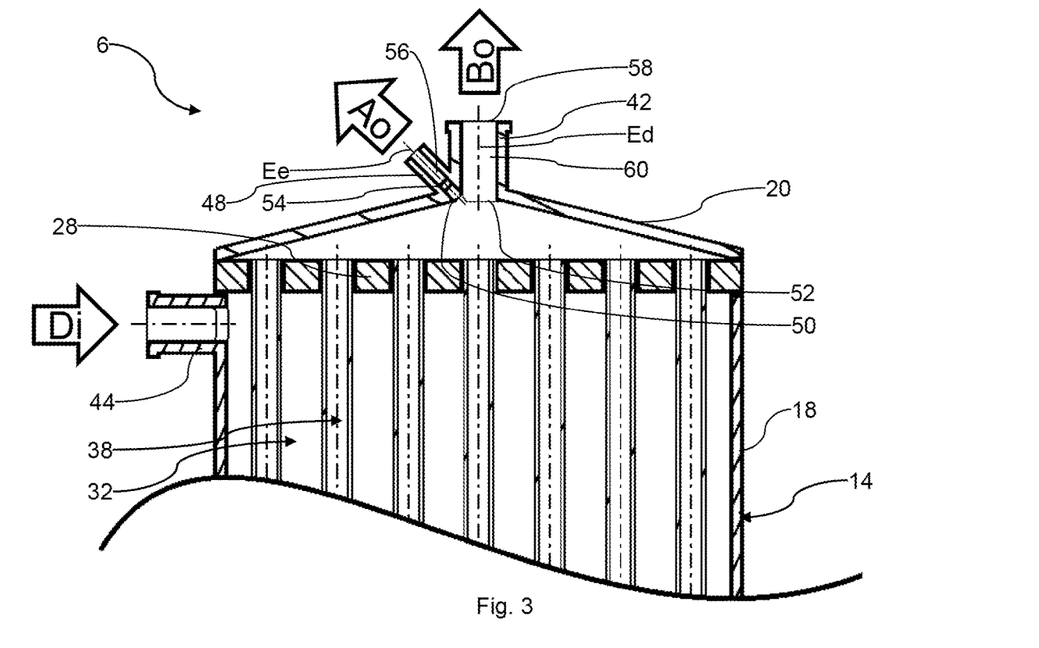
FIG. 3 is a detailed view of a blood outlet side of the dialyzer shown in FIG. 2.

As shown in FIG. 3 in more detail, the blood outlet dialyzer cap 20 has a ventilation outlet 48. The ventilation outlet 48 has the shape of a nozzle or a hollow cylinder and extends with respect to the extension direction Ed of the dialyzer 6 in an angled axis Ee inclined towards the blood discharge port 42. A mouth 50 of the ventilation outlet 48 is immediately adjacent to a mouth 52 of the blood discharge port 42. Inside of the ventilation outlet 48, a ventilation membrane 54 is provided, which closes a channel 56 running inside the ventilation outlet 48 along its extension direction Ee in an air-permeable and waterproof manner.

The dialyzer 6 shown in FIGS. 2 and 3 is intended to be vertically attached to a dialysis device 2 in such a way that the blood supply port 40 is at the bottom and the blood discharge port 42 at the top.

To remove air present in the blood chamber 38 before blood treatment, the blood discharge port 42 or a hose (not shown) attached to the blood discharge port 42 is closed or clamped and saline solution is supplied to the blood chamber 38 via the blood supply port 40. By filling the blood chamber 38 with saline solution, the air previously present in the blood chamber 38 is gradually released from the blood chamber 38 via the ventilation outlet 48 (see arrow "Ao" in FIG. 2). Until the second hollow fiber bundle 28 is reached, air is also largely displaced into the dialysis liquid chamber 32 via the dialysis membrane 30. As soon as the level of the saline solution has reached the second hollow fiber bundle mount 28, most of the air is vented via the ventilation outlet 48. As soon as the level of the saline solution has exceeded the ventilation membrane 54, the air is no longer vented via displacement but only via diffusion.

Figure 4:
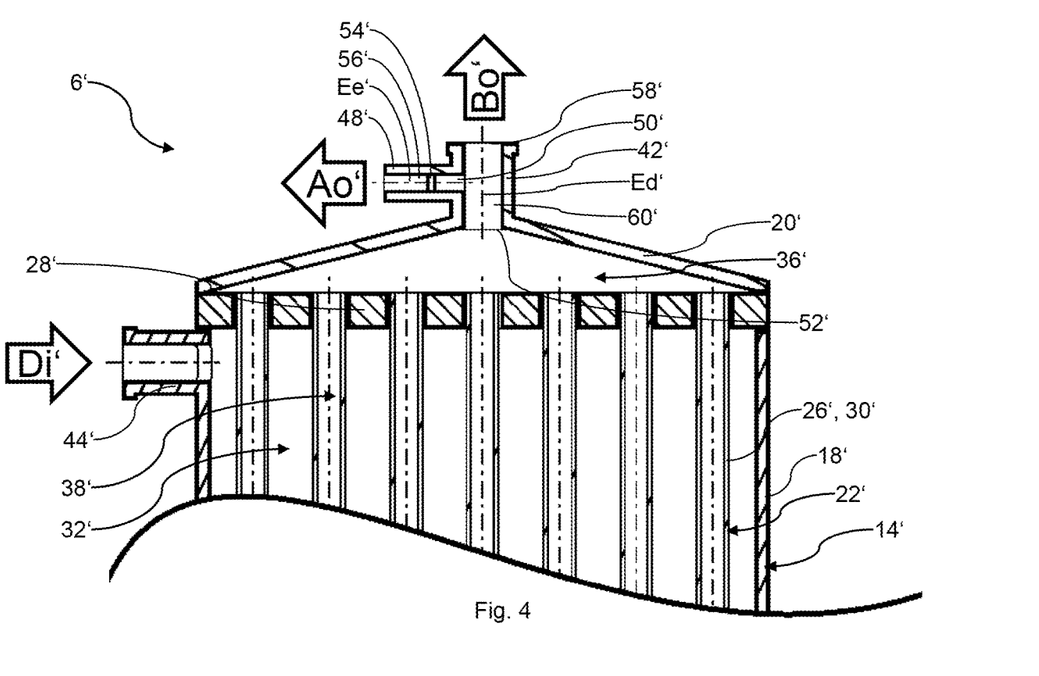
FIG. 4 is a detailed view of a blood outlet side of a dialyzer according to the invention corresponding to FIG. 3 according to a second embodiment.

In order to remove an even larger part of the air present in the blood chamber 38 compared to the first embodiment via the faster displacement, a ventilation outlet 48' is arranged even closer to an exit area 58' with a dialyzer 6' according to a second embodiment shown in FIG. 4. A mouth 50' of the ventilation outlet 48' is thus only in contact with a channel 60' running inside the blood discharge port 42. So that the longitudinal dimension of the dialyzer 6' according to the second embodiment is not greater than the longitudinal dimension of the dialyzer 6 according to the first embodiment, the ventilation outlet 48' is designed in the form of a nozzle or a hollow cylinder which extends in an axis Ee' arranged at right angles with respect to an extension direction Ed' of the dialyzer 6'. Like the ventilation outlet 6 according to the first embodiment, the ventilation outlet 6" according to the second embodiment also has a ventilation membrane 54', which closes a channel 56' running inside the ventilation outlet 48' along its extension direction Ee' in an air-permeable and waterproof manner.

Figure 5:
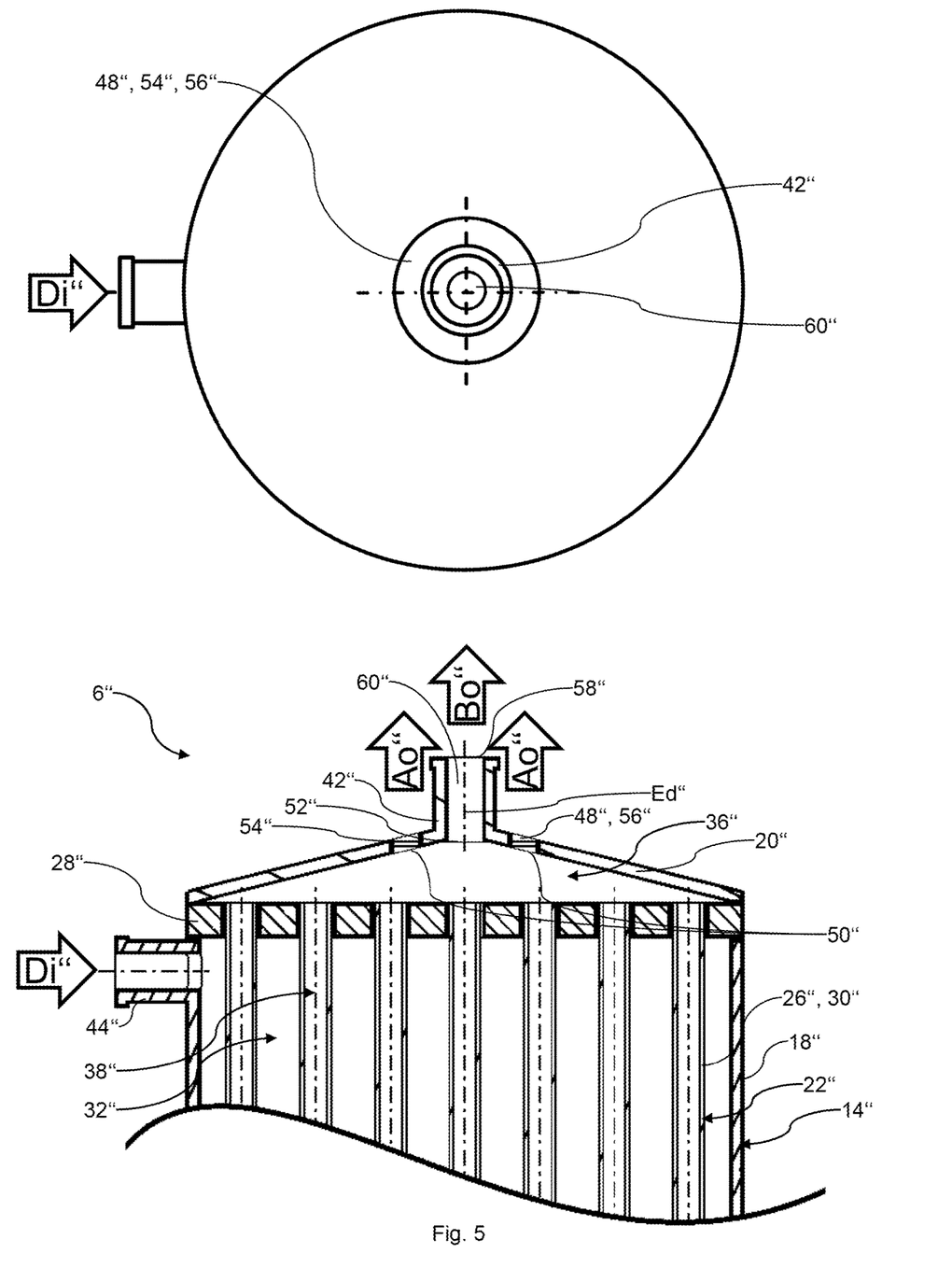
FIG. 5 is a detailed view of a blood outlet side of a dialyzer of the invention according to a third embodiment corresponding to FIG. 3, together with a frontal view.

According to a third embodiment of a dialyzer 6" shown in FIG. 5, a ventilation outlet 48" can be formed on a blood outlet dialyzer cap 20" in such a way that it extends annularly around a blood discharge port 42". In order to ensure the structural integrity of the blood outlet dialyzer cap 20", the annular ventilation outlet 48" may also be formed by several ventilation outlets (not shown) which are annularly arranged around the blood discharge port 42', or webs (not shown) for bridging a corresponding annular groove may be provided in the ventilation outlet 48". A ventilation membrane 54" is provided in the ventilation outlet 48".

Figure 7:
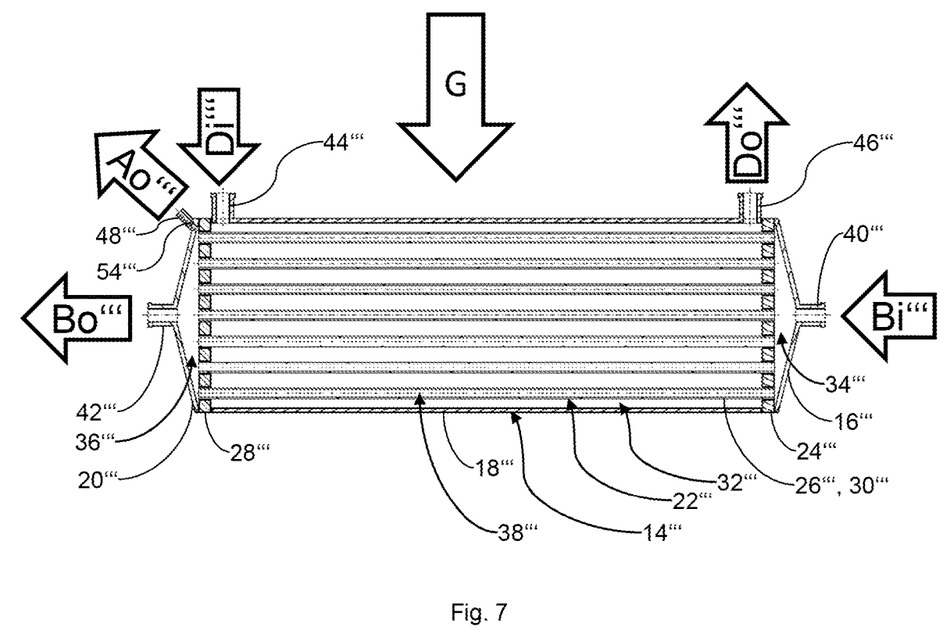
FIG. 7 shows a sectional drawing of a dialyzer of the invention according to a fourth embodiment.
Figure 8:
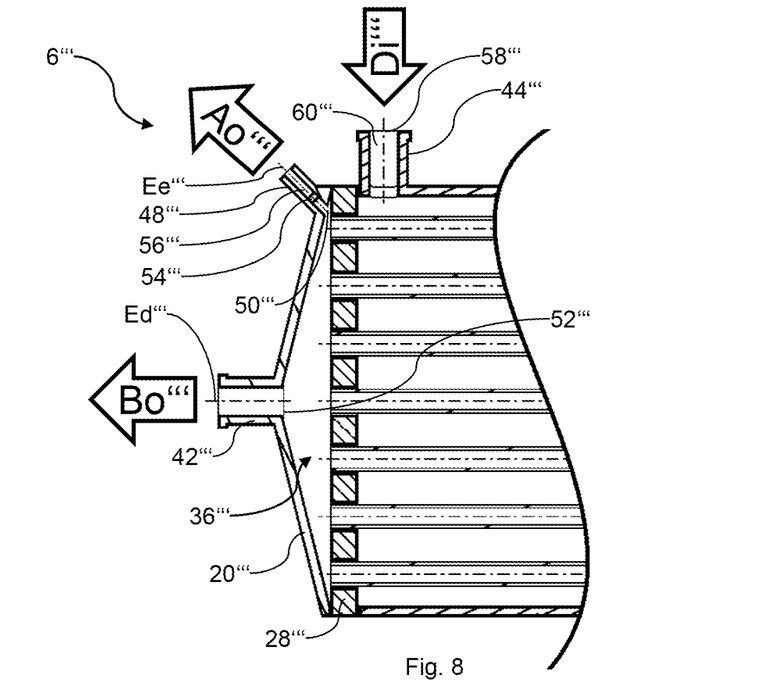
FIG. 8 is a detailed view of a blood outlet side of the dialyzer shown in FIG. 7.

FIGS. 7 and 8 show a dialyzer 6'" according to a fourth embodiment. The dialyzer 6'" is intended to be attached horizontally to a dialysis device 2 as shown in FIG. 6. A ventilation outlet 48'" provided with a ventilation membrane 54'" is arranged at the edge of a blood outlet dialyzer cap 20'". This ensures that the ventilation membrane 54'" is wetted as late as possible when the horizontally mounted dialyzer 6'" is filled.

Figure 9:
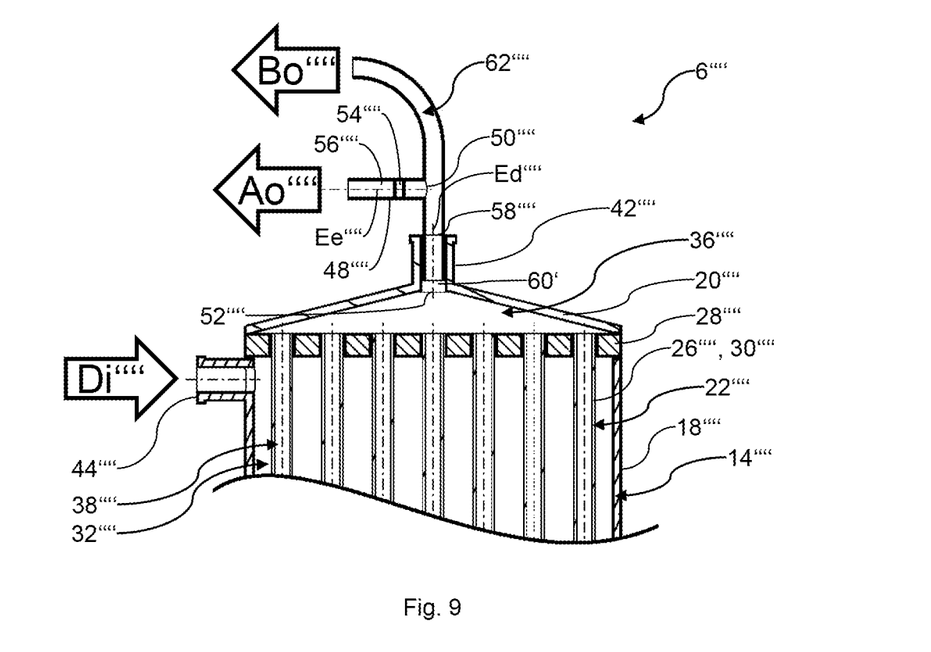
FIG. 9 is a detailed view of a blood outlet side of a dialyzer of the invention corresponding to FIG. 3 according to a fifth embodiment.

FIG. 9 shows a generic dialyzer 6''''. A hose 62'''' is connected to a blood discharge port 42'''' of the dialyzer 6'''', which hose has a ventilation outlet 48'''' with a ventilation membrane 54'''' near the blood discharge port 42''''.

The invention claimed is:

1. A dialyzer for an extracorporeal blood treatment, comprising:
    an elongated dialyzer housing;
    at least one dialysis membrane which separates an internal space of the dialyzer housing into a dialysis liquid chamber provided with a dialysis liquid supply port as well as a dialysis liquid discharge port and into a blood chamber provided with a blood supply port as well as a blood discharge port;
    an additional ventilation outlet which is intended for ventilating the blood chamber, the additional ventilation outlet being formed on the dialyzer housing on or close to an end face thereof and closed; and
    a ventilation membrane that closes the additional ventilation outlet, the ventilation membrane comprising an at least double-ply design, a first ply of the ventilation membrane being formed so as to be hydrophobic and a second ply of the ventilation membrane being formed as a sterile barrier,
    wherein the additional ventilation outlet is provided with respect to a blood flow direction in the blood discharge port between an exit area of the blood discharge port and the dialysis liquid supply port.

2. The dialyzer according to claim 1, wherein the dialyzer housing comprises a dialyzer cap on which the additional ventilation outlet is provided.

3. The dialyzer according to claim 1, wherein the additional ventilation outlet is provided on the blood discharge port.

4. The dialyzer according to claim 1, wherein the dialyzer housing is provided with a nozzle to which a closure for air-tight closing of the additional ventilation outlet is attachable.

5. A dialyzer for an extracorporeal blood treatment, comprising:
    an elongated dialyzer housing;
    at least one dialysis membrane which separates an internal space of the dialyzer housing into a dialysis liquid chamber provided with a dialysis liquid supply port as well as a dialysis liquid discharge port and into a blood chamber provided with a blood supply port as well as a blood discharge port; and
    an additional ventilation outlet which is intended for ventilating the blood chamber, the additional ventilation outlet being formed on the dialyzer housing on or close to an end face thereof and closed,
    wherein the additional ventilation outlet is formed so as to annularly surround the blood discharge port and is provided with respect to a blood flow direction in the blood discharge port between an exit area of the blood discharge port and the dialysis liquid supply port.

6. The dialyzer according to claim 1, wherein the first ply of the ventilation membrane has larger pores and a smaller surface area than the second ply of the ventilation membrane.

7. A dialysis device for an extracorporeal blood treatment, comprising a dialyzer according to claim 1.

8. The dialysis device according to claim 7, wherein the dialyzer is attached to the dialysis device in such a manner that the additional ventilation outlet, when the dialysis device is installed ready for operation, is arranged so as to be at least partially above the dialysis liquid supply port in a direction of gravitational acceleration.

9. The dialysis device according to claim 7, wherein the dialyzer is attached to the dialysis device in such a manner that the ventilation outlet, when the dialysis device is installed ready for operation, is arranged so as to be at least partially above the blood chamber in a direction of gravitational acceleration.

10. A dialysis device for an extracorporeal blood treatment, comprising:
    a dialyzer;
    an elongated dialyzer housing;
    at least one dialysis membrane which separates an internal space of the dialyzer housing into a dialysis liquid chamber provided with a dialysis liquid supply port as well as a dialysis liquid discharge port and into a blood chamber provided with a blood supply port as well as a blood discharge port; and
    a waterproof and air-permeable ventilation membrane which in at least one portion forms a surrounding wall of a hose connected to the blood discharge port, so that, when filling the blood chamber with a liquid, any air present in the blood chamber escapes through the ventilation membrane until the blood chamber is completely filled with the liquid.

11. The dialysis device according to claim 8, wherein the dialyzer is attached to the dialysis device in such a manner that a liquid conveyed through the blood chamber flows diametrically against the direction of gravitational acceleration.

12. The dialysis device according to claim 7, wherein the dialyzer is attached to the dialysis device in such a manner that a liquid conveyed through the blood chamber flows perpendicular to a direction of gravitational acceleration.

\* \* \* \* \*